United States Patent [19]

Jaedicke

[11] Patent Number: 4,727,188

[45] Date of Patent: * Feb. 23, 1988

[54] PREPARATION OF O,O'-DITHIODIBENZAMIDES

[75] Inventor: Hagen Jaedicke, Ludwigshafen, Fed. Rep. of Germany

[73] Assignee: BASF Aktiengesellschaft, Fed. Rep. of Germany

[*] Notice: The portion of the term of this patent subsequent to Jan. 15, 2002 has been disclaimed.

[21] Appl. No.: 717,010

[22] Filed: Mar. 28, 1985

[30] Foreign Application Priority Data

Mar. 28, 1984 [DE] Fed. Rep. of Germany ....... 3411385

[51] Int. Cl.$^4$ .................. C07C 102/00; C07C 103/76; C07C 103/24; C07C 103/78
[52] U.S. Cl. .................................. 564/154; 564/163; 564/166; 564/167; 564/168
[58] Field of Search ................... 564/154; 260/544 S; 562/431; 568/25

[56] References Cited

U.S. PATENT DOCUMENTS 3,736,280  5/1973  Grivas .
3,786,150  1/1974  Lee et al. .
4,295,887 10/1981  Buckley et al. .
4,493,802  1/1985  Jaedicke et al. ................... 260/507

OTHER PUBLICATIONS

P. A. S. Smith, *Open-Chain Nitrogen Compounds,* 1966, pp. 100 and 296.
Theilheimer, Synthetic Methods of Organic Chemistry, vol. 6, p. 216, (1952).
Chemische Berichte, vol. 99, p. 2566, (1966).

*Primary Examiner*—Charles F. Warren
*Assistant Examiner*—Carolyn S. Greason
*Attorney, Agent, or Firm*—Keil & Weinkauf

[57] ABSTRACT o,o'-Dithiodibenzamides of the formula

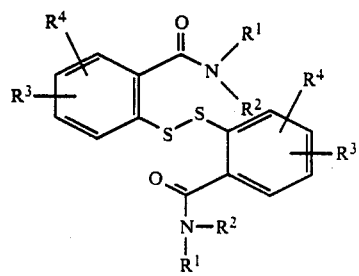

where $R^1$ and $R^2$ are each hydrogen, alkyl or phenyl, $R^3$ is hydrogen, halogen, nitro, methyl or methoxy, and $R^4$ has the same meanings as $R^3$, are prepared by nitrosating an anthranilamide of the formula

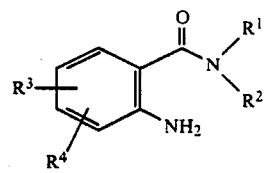

and reacting the product with sulfur dioxide in the presence of copper or a copper salt.

4 Claims, No Drawings

PREPARATION OF O,O'-DITHIODIBENZAMIDES

The present invention relates to a process for the preparation of o,o'-dithiodibenzamides from anthranilamides with nitrous acid and sulfur dioxide.

o,o'-Dithiobenzamides have been disclosed (U.S. Pat. No. 3,736,280, U.S. Pat. No. 2,663,616, DE-B-2,615,662 and U.S. Pat. No. 3,786,150). It is known that these compounds can be prepared by reacting substituted o,o'-dithiodiphenyldicarboxylic acid chlorides with ammonia or amines (H. Boshagen, Chem. Ber. 99 (1966), 2566; DE-B-2,615,662). This process has the disadvantage that the o,o'-dithiodiphenyldicarboxylic acid chlorides are difficult to obtain.

I have found that o,o'-dithiodibenzamides of the formula

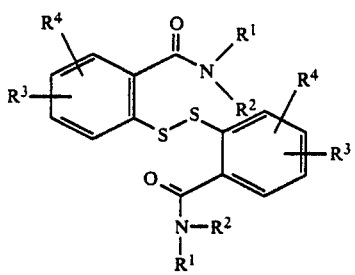

where $R^1$ and $R^2$ are each hydrogen, alkyl of 1 to 4 carbon atoms or phenyl, $R^3$ is hydrogen, chlorine, bromine, fluorine, nitro, methyl or methoxy, and $R^4$ has the same meanings as $R^3$ and is identical to or different from $R^3$, are obtained in a simple manner if an anthranilamide of the formula

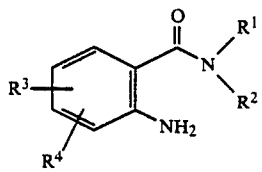

where $R^1$, $R^2$, $R^3$ and $R^4$ have the above meanings, is nitrosated in water, and the product is reacted with sulfur dioxide in the presence of copper, a copper compound or a copper salt. In this way, the desired end product is obtained from the simple starting material anthranilamide, which is readily obtainable from isatoic anhydride with ammonia or an amine.

Alkyl of 1 to 4 carbon atoms is, for example, methyl, ethyl, propyl, isopropyl, butyl, sec.-butyl or tert.-butyl.

Nitrosation is, for example, the reaction with nitrous acid, a nitrite (eg. amyl nitrite) or a nitrous gas.

An example of a copper compound is copper oxide, while a copper salt is, for example, copper(II) chloride, copper(II) sulfate or copper(II) nitrate.

To carry out the reaction with nitrous acid, for example, sodium nitrite and a mineral acid, eg. hydrochloric acid or sulfuric acid, are used. The process according to the invention can be represented by, for example, the following scheme, in which X is an anion of a mineral acid.

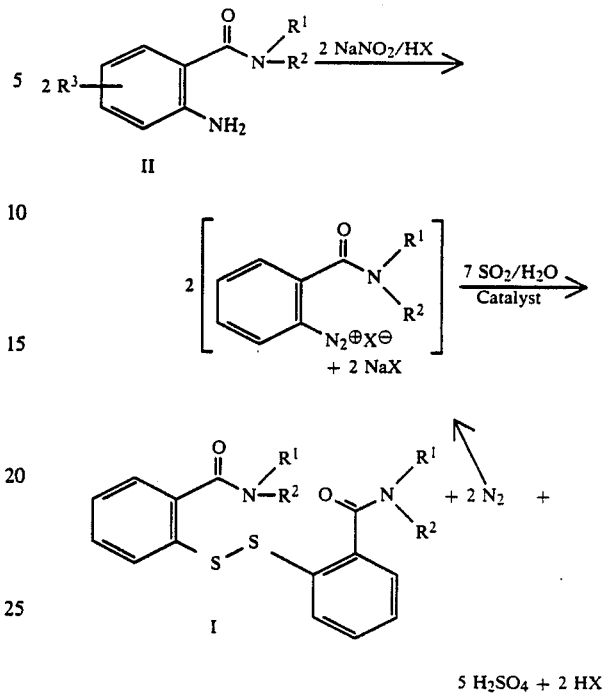

The catalyst can be, for example, a Cu salt (chloride, sulfate or nitrate) or metallic Cu. The Cu salt or Cu may also be combined with an alkali metal iodide. For example, from 0.001 to 0.1, preferably 0.01, mole of Cu salt is used per mole of the compound II, and, for example, the same amount of alkali metal iodide is used when the mixture is employed. Elemental iodine and hydrogen iodide are also suitable for the mixture.

The reaction with nitrous acid is carried out at, for example, from 0° to 40° C., preferably from 5° to 10° C., and decomposition is effected at, for example, from 10° to 100° C., preferably from 40° to 70° C. For example, the $SO_2$ together with the diazonium salt can be added to the catalyst, or the $SO_2$ can be added to the mixture of the diazonium salt and the catalyst.

The Examples which follow illustrate the process.

EXAMPLE 1

108.8 g of anthranilamide were suspended in 975 g of 30% strength by weight hydrochloric acid, the suspension was cooled to 5° C., and 223.5 g of a 25% strength solution of $NaNO_2$ in water were added dropwise in the course of 30 minutes. The mixture was stirred for a further 30 minutes at 5° C., and the cooled solution was then pumped, in the course of 5 hours, into a solution prepared from 340 ml of $H_2O$, 1.4 g of $CuCl_2.2H_2O$, 1.3 g of KI and 5 g of $SO_2$ (catalyst solution). The catalyst solution was heated to 50° C. beforehand. Simultaneously with the nitrosated anthranilamide, a stream of 46 g/hour of $SO_2$ was passed into the reaction mixture. When the addition of the nitrosated anthranilamide was complete, the suspension of o,o'-dithiodibenzamide was stirred for a further hour at 55° C. and then cooled, and the product was filtered off under suction and dried. 110.5 g of pure o,o'-dithiodibenzamide of melting point 252°–253° C. were obtained.

EXAMPLE 2 o,o'-Dithiodibenzoic acid diisopropylamide 178 g of anthranilic acid isopropylamide were suspended in 1,100 g of 30% strength hydrochloric acid, and 173 g of a 40% strength aqueous solution of $NaNO_2$ were added dropwise at from 10° to 15° C., the temperature not exceeding 15° C. The resulting suspension was pumped uniformly into a stirred decomposition vessel in the course of 2 hours, the vessel containing a solution of 3.5 g of $CuCl_2.2H_2O$ and 1.5 g of KI in 100 ml of water. 192 g of $SO_2$ were passed into the decomposition vessel during the first hour of pumping, and 96 g of $SO_2$ in the course of the second hour. The temperature during this period remained constant at 55° C. When the addition was complete, stirring was continued for one hour at 95° C., after which the mixture was cooled. 163 g of o,o'-dithiodibenzoic acid diisopropylamide of melting point 244°–245° C. (literature mp. 245° C.; F. Gialdi, R. Pouci and A. Baruffini, Farmaco Ed. Sci. 14 (1959), 648) were obtained.

EXAMPLE 3

108.8 g of anthranilamide were dissolved in 1,100 g of 70% strength by weight $H_2SO_4$, 223.5 g of 25% strength aqueous $NaNO_2$ solution were added dropwise at from 25° to 30° C., and the mixture was then stirred for one hour at 25° C. The solution was run, in the course of four hours, into a vessel which was thermostatted at 60° C. and contained a solution of 1.1 g of KI and 2.1 g of $CuSO_4.5H_2O$ in 150 ml of $H_2O$. Simultaneously with the addition of the solution of diazonium salt, 230 g of $SO_2$ gas were passed into the vessel. When the addition was complete, the suspension was stirred for a further hour at 60° C., after which the product was filtered off under suction. 113.4 g of pure o,o'-dithiodibenzamide of melting point 252°–253° C. were obtained.

I claim:

1. A process for the preparation of an o,o'-dithiodibenzamide of the formula

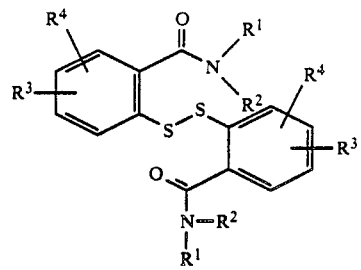

where $R^1$ and $R^2$ are each hydrogen, alkyl of 1 to 4 carbon atoms or phenyl, $R^3$ is hydrogen, chlorine, bromine, fluorine, nitro, methyl or methoxy, and $R^4$ has the same meanings as $R^3$ and is identical to or different from $R^3$, wherein an anthranilamide of the formula

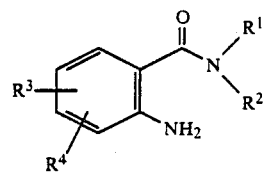

where $R^1$, $R^2$, $R^3$ and $R^4$ have the above meanings, is nitrosated in water as a solvent at a temperature of from 0° to 40° C., and the product is reacted at a temperature of from 10° to 100° C. in water with sulfur dioxide in the presence of copper, a copper compound or a copper salt derived from bivalent copper.

2. A process as described in claim 1, wherein the reaction with sulfur dioxide is carried out in the presence of a mixture of a copper salt and iodine, hydrogen iodide or an alkali metal iodide.

3. A process as described in claim 1, wherein the reaction is carried out in the presence of iodine ions.

4. A process as described in claim 1, wherein the reaction with sulfur dioxide is carried out in the presence of a copper salt derived from bivalent copper.

* * * * *